United States Patent
Elliott et al.

[19]

[11] Patent Number: 5,810,829
[45] Date of Patent: Sep. 22, 1998

[54] POSTERIOR STABILIZED/CONSTRAINED REAMER GUIDE

[75] Inventors: Scott Elliott; Jennifer J. Lackey, both of Memphis; Steve M. Tammi, Collierville, all of Tenn.; Leonard J. Tokish, Jr., Palm Desert, Calif.

[73] Assignee: Smith & Nephew, Inc., Memphis, Tenn.

[21] Appl. No.: 804,247

[22] Filed: Feb. 21, 1997

Related U.S. Application Data

[60] Provisional application No. 60/011,994 Feb. 21, 1996.
[51] Int. Cl.[6] .................................................. A61B 17/56
[52] U.S. Cl. ............................... 606/80; 606/88; 606/96
[58] Field of Search ................................. 606/88, 89, 87, 606/86, 96, 97, 98, 80, 79, 81, 82, 83, 84, 85

[56] References Cited

U.S. PATENT DOCUMENTS

5,423,827  6/1995  Mumme et al. ........................... 606/96
5,454,816  10/1995 Ashby ........................................ 606/88
5,514,140  5/1996  Lackey ....................................... 606/80
5,593,411  1/1997  Stalcup et al. ............................ 606/88
5,658,292  8/1997  Axelson, Jr. et al. .................... 606/86

*Primary Examiner*—Guy V. Tucker
*Attorney, Agent, or Firm*—Pravel, Hewitt & Kimball

[57] ABSTRACT

A posterior stabilized/constrained reamer guide is provided that enables a surgeon to prepare a patient s distal femur to receive either a posterior stabilized or a constrained type femoral component. The instrument guide has an opening the largest anterior to posterior housing size. For example, a constrained housing has a longer anterior to posterior dimension than a posterior stabilized housing. The apparatus of the present invention provides an improved reamer guide that addresses differences in housing sizes and necessary bone removal. The apparatus provides a housing guide that accepts either a posterior stabilized collet or a constrained collet. Each of the collets accepts a rotary reamer or a box chisel. During surgery, the reamer is first used to form a cylindrically-shaped or oval shaped cut. The box chisel then removes additional bone to create a rectangular or squared opening. This insures that only the necessary bone is removed for each housing depending upon the one selected by the surgeon.

24 Claims, 12 Drawing Sheets

SECTION D-D
FIGURE 19

SECTION B-B
FIGURE 17

VIEW C-C
FIGURE 18

POSTERIOR STABILIZED/CONSTRAINED REAMER GUIDE

CROSS-REFERENCE TO RELATED APPLICATIONS

Priority of U.S. Provisional patent application Ser. No. 60/011,994, filed Feb. 21, 1996, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to surgical orthopaedic instrumentation, particularly cutting instrumentation for use in preparing the distal femur of a patient in preparing the distal to receive a femoral prosthesis wherein one housing preparation guide that accommodates for the differences in housing size between the posterior stabilized and constrained type femoral components.

2. General Background of the Invention

Posterior stabilized and constrained femoral components have a cam housing in between the condyles. Bone from the distal femur must be removed to accommodate for this type of housing. The housing sizes differ for posterior stabilized and constrained type femoral components. Therefore, a different amount of bone needs to be removed for each of these types of femoral components.

Two separate instruments are presently required, one to prepare for a posterior stabilized type component and another to prepare for a constrained type component.

BRIEF SUMMARY OF THE INVENTION

The present invention provides an instrument guide apparatus that can prepare for both the posterior stabilized type femoral component and the constrained type femoral component.

The instrument guide of the present invention has an opening the largest A/P (anterior and posterior) housing size. For example, the constrained housing has a longer A/P dimension than the posterior stabilized housing. Therefore, the A/P opening would be sized for the constrained component. The distal height of the housings are also different between the posterior stabilized and constrained components.

To adds these differences in housing sizes and necessary bone removal, an improved orthopaedic cutting instrument is provided.

The present invention provides a housing guide that accepts a first posterior stabilized type collet and a second constrained type collet to limit the amount of bone removed in the A/P dimension and in depth.

Each of these collets accepts a reamer and a box chisel. During surgery, the reamer and then the box chisel removes the bone from the distal femur. This ensures that only the necessary bone be removed for each housing.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
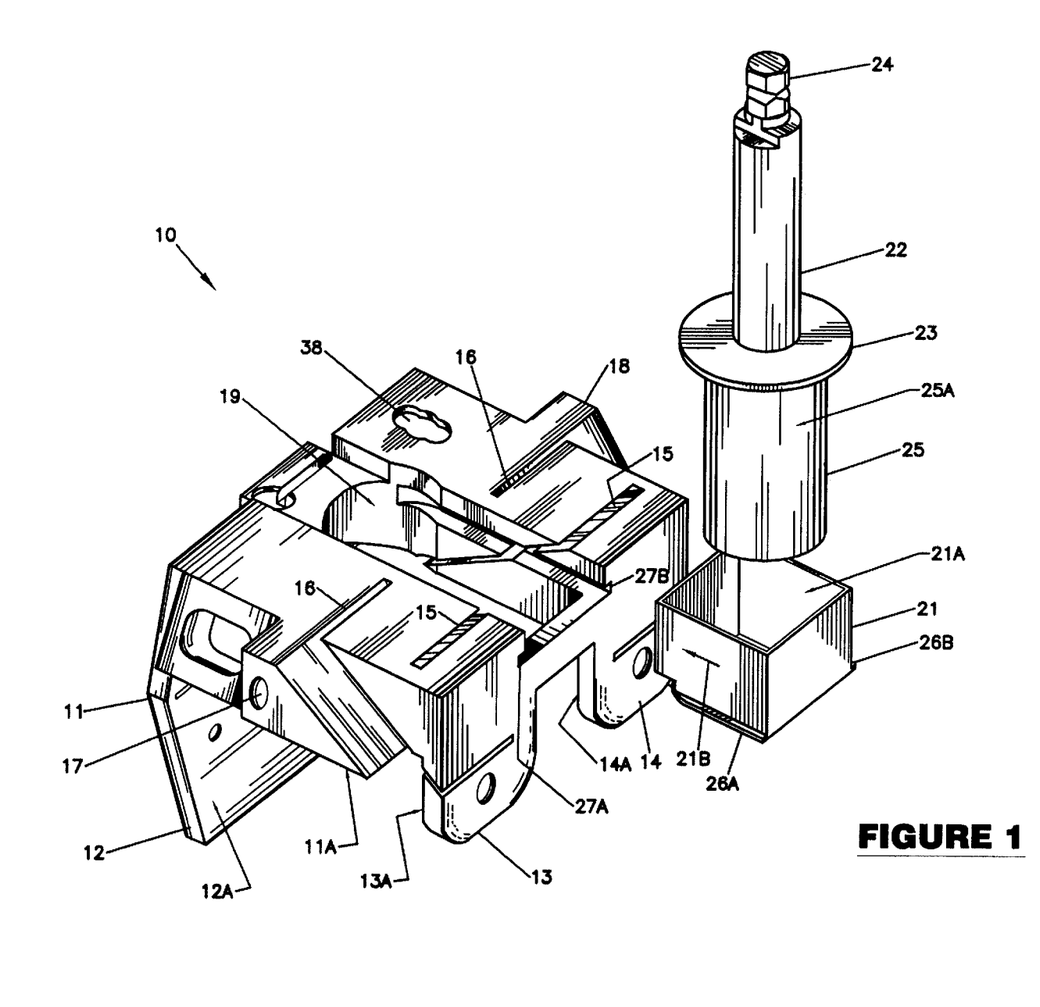
FIG. 1 is the perspective exploded view of the preferred embodiment of the apparatus of the present invention.
Figure 2:
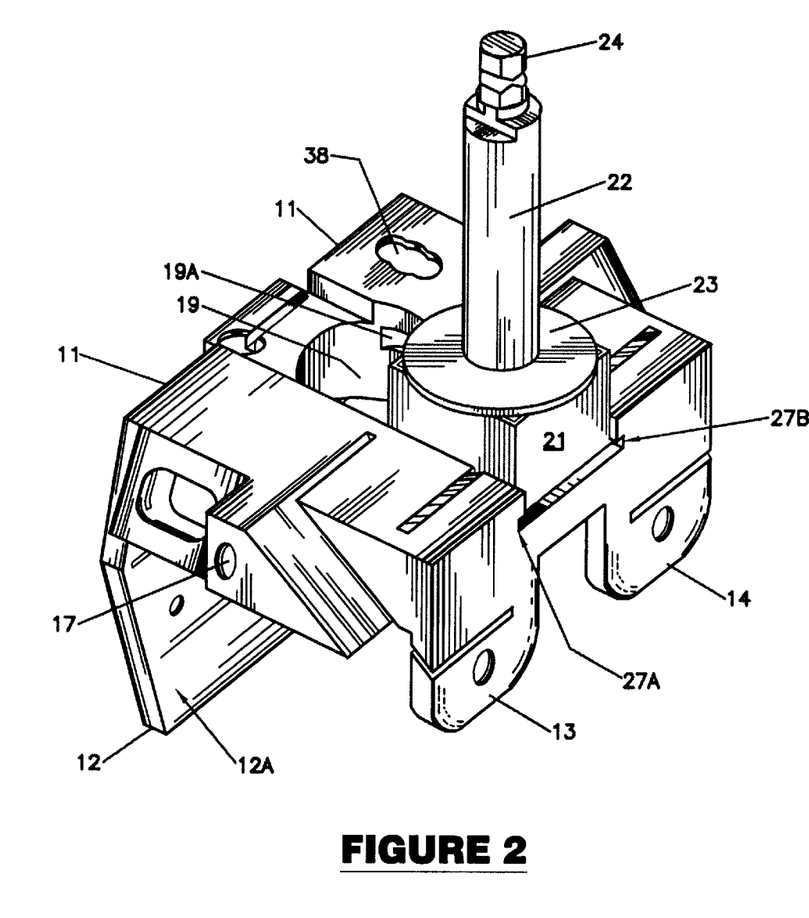
FIG. 2 is a perspective view of the preferred embodiment of the apparatus of the present invention.
Figure 3:
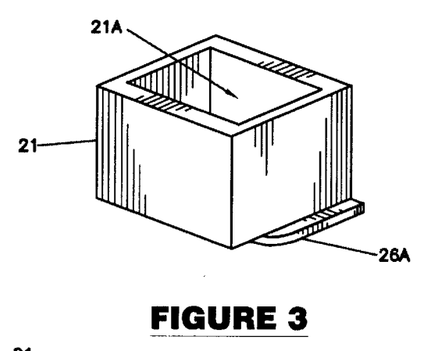
FIGS. 3–7 are various views of the constrained collet portion of the preferred embodiment of the apparatus of the present invention.
Figure 4:
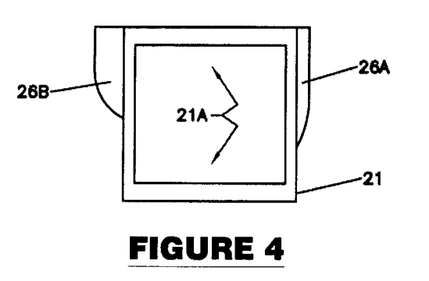
Figure 5:
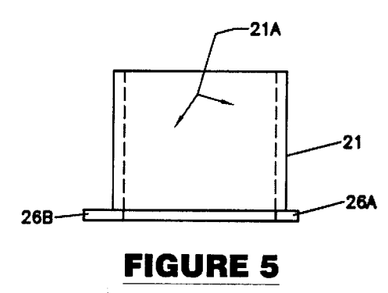
Figure 6:
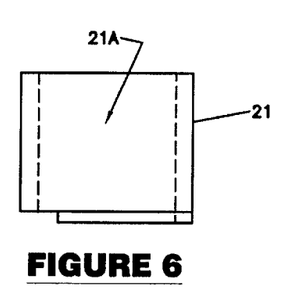
Figure 7:
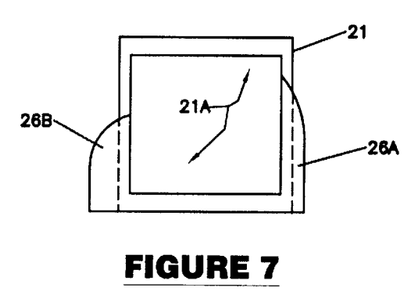

FIGS. 1–7 show the preferred embodiment of the apparatus of the present invention designated generally by the numeral 10. Cutting block body 11 is shown in FIGS. 1–2 with a collet 21 that can be, for example, a constrained collet for supporting a reamer 22 while making one type of cut on the patient's distal femur in order to receive a femoral prosthesis. In FIGS. 8–9 and 20–23, a collet 20 that could be a posterior stabilized collet is shown for use with the same reamer 22 that is used in FIGS. 1–2 with collet 21. Either collet 20 or 21 can receive a box chisel that is used to shave corners of a cut that is initially formed with reamer 22.

In FIGS. 10–11 and 12–19, there is shown a modular stem portion 30 that can be affixed to the block body 11 preferably for use in revision cases.

FIGS. 20–23 show the posterior stabilized collet portion of the preferred embodiment of the apparatus of the present invention.

FIGS. 24–27 show various views of the instrument block body 11. The cutting block body 11 can be attached to the patient's cut distal femur using bone spikes for example that are placed through openings at 17, 18.

In FIG. 1, cutting instrument 10 includes a block body 11 having an anterior flange 12 and a pair of posterior flanges 13–14. The anterior flange 12 engages a patient's anteriorly cut distal femur. Posterior flanges 13–14 engage posterior cuts made on the patient's posterior condylar portions by a surgeon. During surgery, a surgeon first makes anterior and posterior cuts that are generally parallel or slightly angled to each other and a distal cut that is generally perpendicular to the anterior and posterior cuts. Block body 11 is then attached to this surgically cut distal femur. Block body 11 provides a pair of diagonally anterior/posterior extending chamfer cutting slots 15, 16.

A central open area 19 accepts either of two different collets 20 or 21 depending upon the type of femoral prosthesis to be implanted. The collet 20 is an example of a posterior stabilized or "P/S" collet. The collet 21 is an example of a constrained collet.

A rotary reamer 22 is preferably sized and shaped to fit either of the collets 20 or 21. The reamer 22 is shown in FIG. 1 as having an annular stop 23 that controls the depth of cut as the stop 23 engages the upper surface of the selected collet 20 or 21. Once the reamer cuts into the distal femur, a cylindrical or oval-shaped cut is formed. A box chisel can then be used to complete a square or rectangular cut by tracking the walls of the selected collet 20 or 21 at the open center 20A or 21A portion thereof.

Reamer 22 further includes an interface 24 for connection with a motor drive such as a drill. The reamer 22 provides a cutting end portion 25 that can include both distal cutting members and peripheral cutting members placed on the cylindrical surface 25A.

Collet 21 provides a pair of spaced apart flanged rails 26A, 26B that engage correspondingly sized and shaped slots 27A–27B on block body 11 so that the collet 21 can slide in the direction of arrow 21B in FIG. 1.

Block body 11 has flat surfaces 11A, 12A, 13A and 14A for engaging the patient's distal femur once it has been cut by a surgeon to provide flat cut surfaces, namely distal, anterior and posterior cut surfaces. The surface 12A engages an anterior cut surface of the femur. The surfaces 13A, 14A engage posterior cut surfaces of the femur. The surface 11A engages the patient's distal femoral cut surface.

Collet 21 can slide in the direction of arrow 21B upon the slotted portions 27A, 27B of block body 11. Slotted portions 27A, 27B are engaged by the flanged rail portions 26A, 26B of collet 21. This sliding of collet 21 can be done simultaneously while reaming of the distal femur with reamer 22 to form an oval shaped cut.

The reamer cylindrical portion 25 is placed within the open center 21A of collet 21. The reamer 22 then extends down into the patient's bone tissue during cutting until the stop 23 engages the upper edge of collet 21 (see FIG. 2). The open portion 21A is open at the top and at the bottom so that the reamer 22 can pass through center 21A of the collet 21 and into the underlying bone tissue during a reaming of the underlying bone tissue.

The slots 27A, 27B are sized and shaped to limit travel of the collet 21 and thus limit the length of a reamed cut in the anterior-posterior inventions in the distal femur. The slots 27A, 27B includes an end portion that functions as a stop for limiting travel of the collet 21 in the direction of arrow 21B.

In FIG. 2, the collet 21 and its reamer 22 are shown in operating position, mounted within the open portion 19 of block body 11. Collet 21 is shown in more detail in FIGS. 3–7. Slots 27A, 27B are positioned relative to surface 11A to address reamer depth for each size.

The open portion 19 and slots 27A, 27B are sized and shaped to limit travel of the collet 21 and thus limit the length of a reamed cut formed in the distal femur. The open slot area 19 includes a stop end portion 19A that functions as a stop for limiting travel of the collet 21 in the direction of arrow 21B. In FIG. 2, the collet 21 and its reamer 22 are shown in operating position, mounted within the open portion 19 of block 11. Collet 21 is shown in more detail in FIGS. 3–7.

In FIGS. 8–9 and 20–23, a second collet 20 is shown. The collet 20 can be for example a posterior stabilized collet as opposed to constrained collet 21. The posterior stabilized collet 20 attaches to slot 38 of block body 11. Collet 20 has a stud 39 that fits slot 38. The length of slot 38 defines the length of travel of collet 20. Sides 20B, 20C of collet 20 register against the block body 11 at open portion 19.

Figure 8:
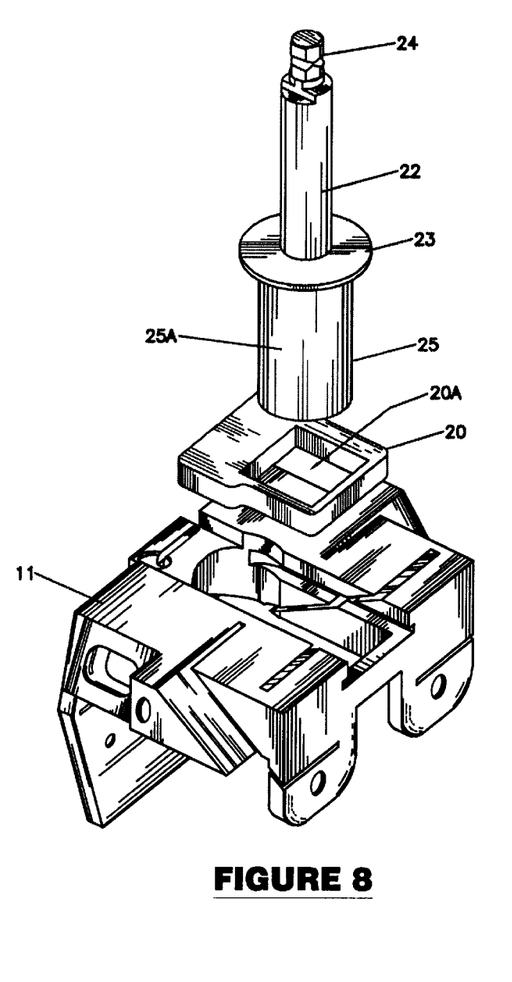
FIG. 8 is an exploded perspective view of the preferred embodiment of the apparatus of the present invention showing the posterior stabilized collet.
Figure 9:
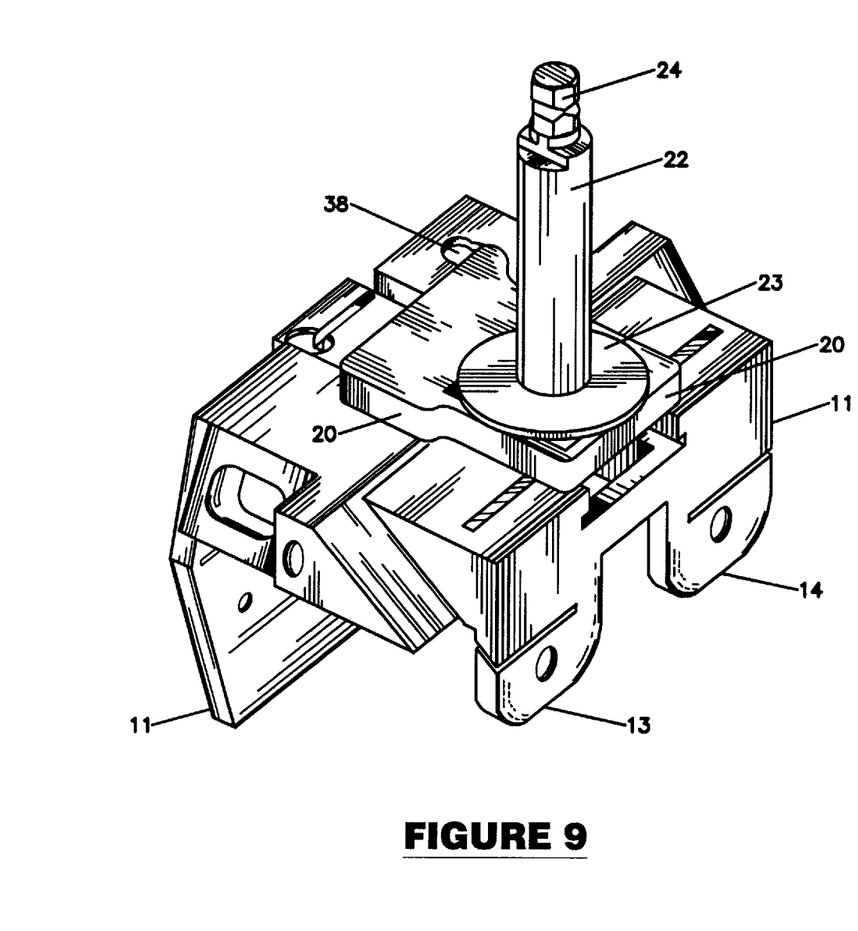
FIG. 9 is a perspective view of the preferred embodiment of the apparatus of the present invention shown with the posterior stabilized collet.

Collet 20 has an open center 20A as shown through which reamer 22 can pass. In order to assemble the collet 20 to the block body 11, the user places the stud 39 into slot 38. The collet 20 can then slide relative to the block body 11 in an anterior to posterior direction.

The present invention allows the connection of modular stems to the instrument block body 11 such as could be of help in revision cases. In FIGS. 10–19, modular stem 30 is shown. The stem 30 has a pair of threaded fasteners 31 that can be used to attach the stem to an internally threaded opening 29 of block body 11. Keys 33 of modular stem 30 register in a correspondingly shaped slot 28 on block body 11, and depending on the stem 30 orientation desired for left or right femurs. As the stem is angled in the M-L dimension, the modular stem 30 can be placed into the block angling the appropriate direction depending on whether or not a left or right knee is being replaced.

Figure 10:
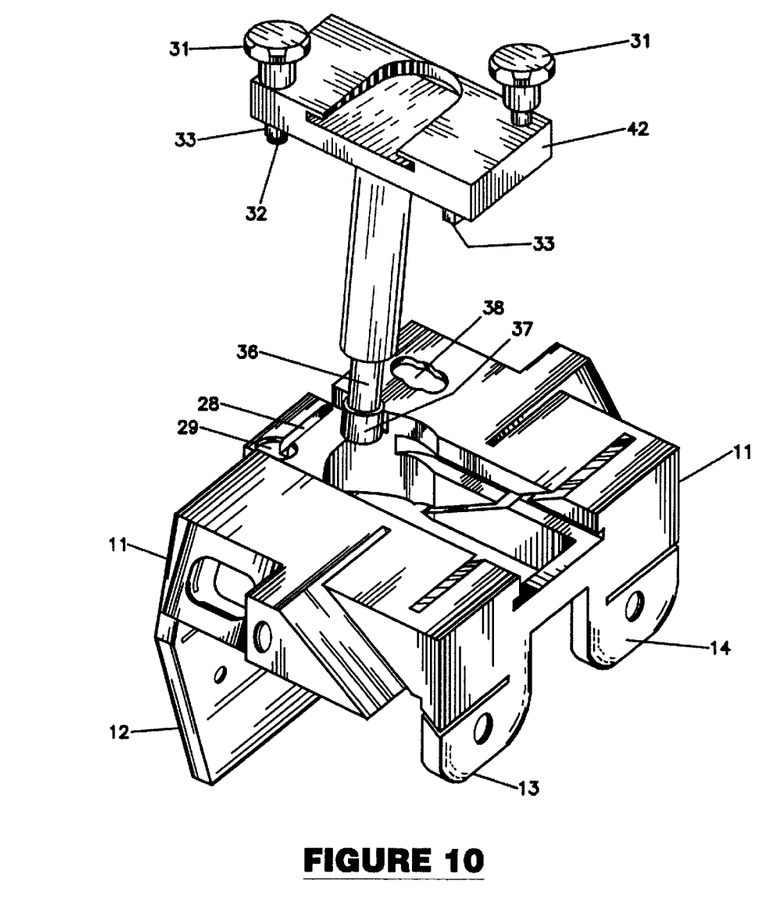
FIG. 10 is an exploded perspective view of the preferred embodiment of the apparatus of the present invention showing the block body and modular stem portions thereof.

In FIGS. 12–19, there can be seen a pair of keys 33 and a pair of cylindrical openings 41 through which threaded fasteners 31 can pass. As shown in FIG. 10, the stem 30 has a rectangular portion 42 that carries two threaded fasteners 31. Each threaded fastener 31 extends through an opening 41 in the rectangular member 42, providing an externally threaded end 32 for engaging the internally threaded opening 29 of block body 11. A key 33 engages slot 28 of block body 11 upon assembly of stem 30 to block body 11. Two keys 33 and two cylindrical openings 41 are provided for a pair of threaded fasteners 31 so that the stem 30 can be used for both right and left knees. The user simply rotates the stem 30 one hundred eighty degrees (180°) when moving from one knee to the other knee to achieve proper orientation with the patient's intramedullary canal.

Figure 11:
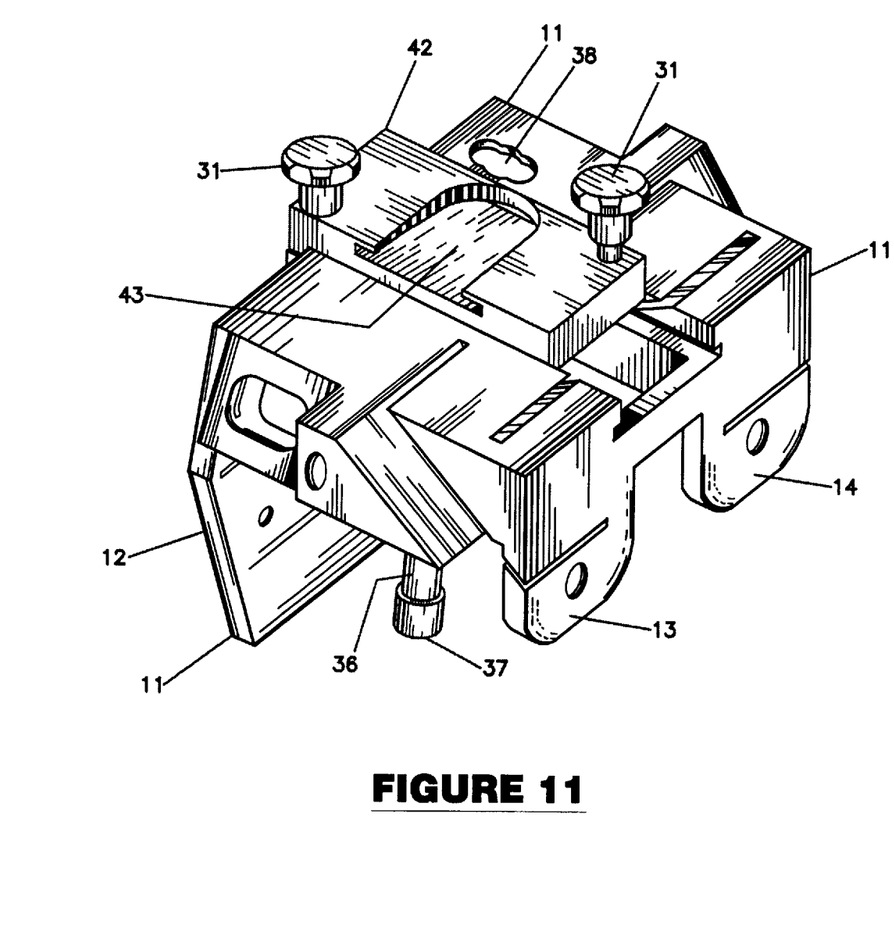
FIG. 11 is a perspective view of the preferred embodiment of the apparatus of the present invention shown in use with the modular stem portion thereof.
Figure 12:
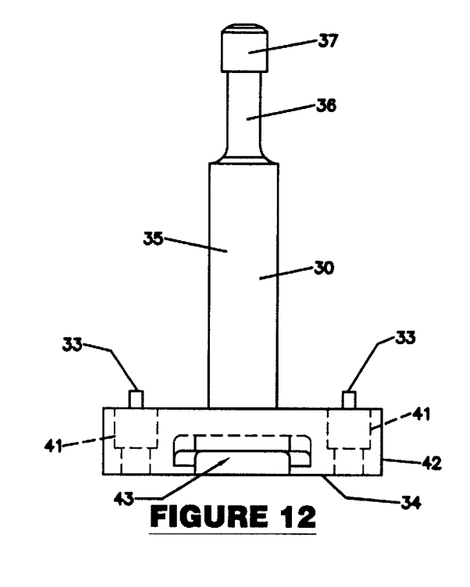
FIGS. 12–13 are elevational views of the modular stem of FIGS. 10–11.
Figure 13:
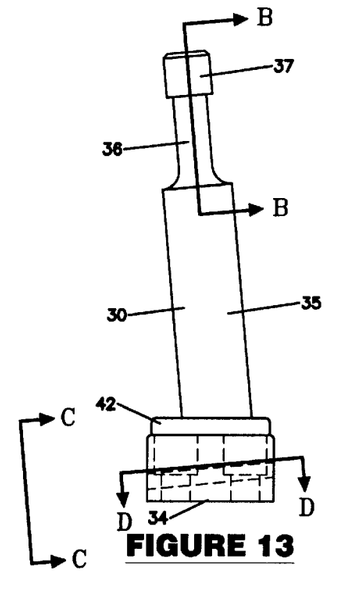
Figure 14:
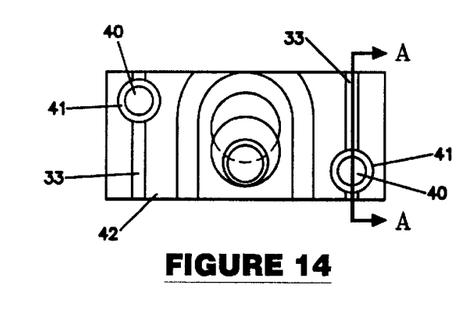
FIG. 14 is a top view of the modular stem of FIGS. 10–11.
Figure 15:
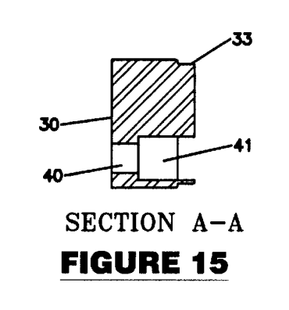
FIG. 15 is a sectional view taken along lines A—A of FIG. 14.
Figure 16:
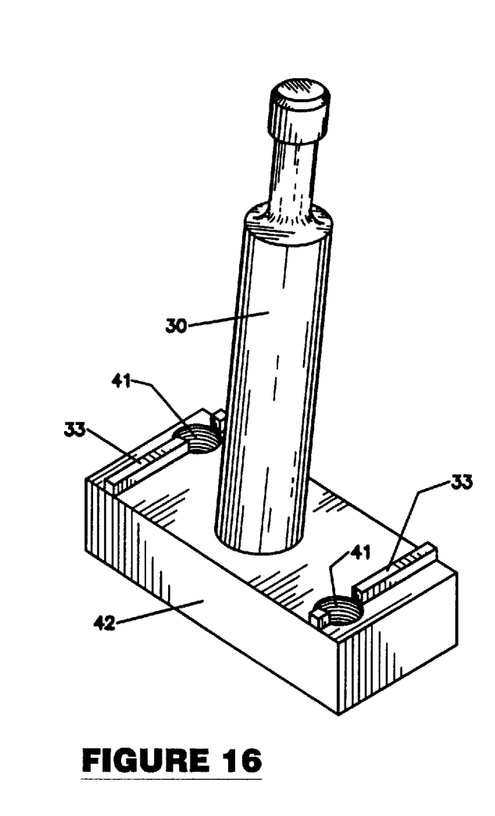
FIG. 16 is a perspective view of the modular stem of FIGS. 10–11.
Figure 17:
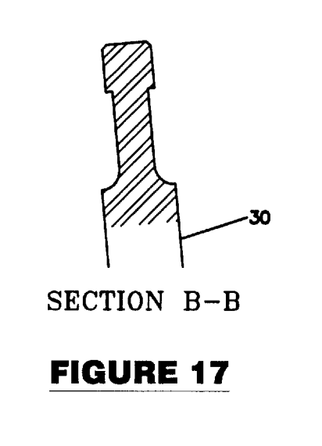
FIG. 17 is a sectional view taken along lines B—B of FIG. 13.
Figure 18:
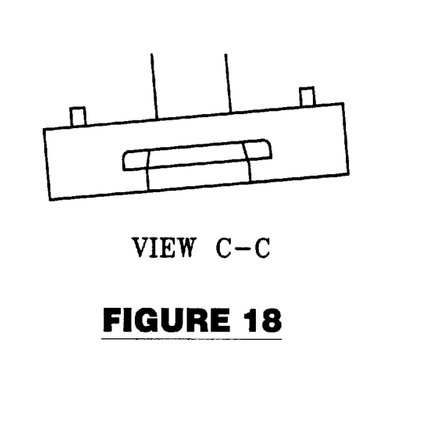
FIG. 18 is an end view taken along lines C—C of FIG. 13.
Figure 19:
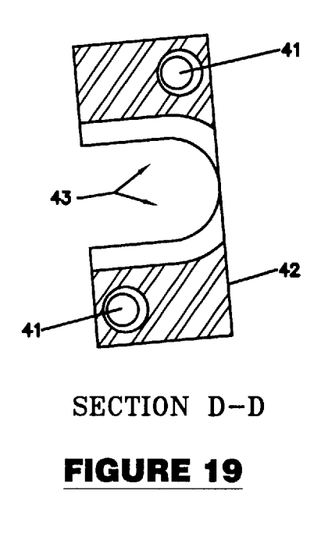
FIG. 19 is a sectional view taken along lines D—D of FIG. 13.
Figure 20:
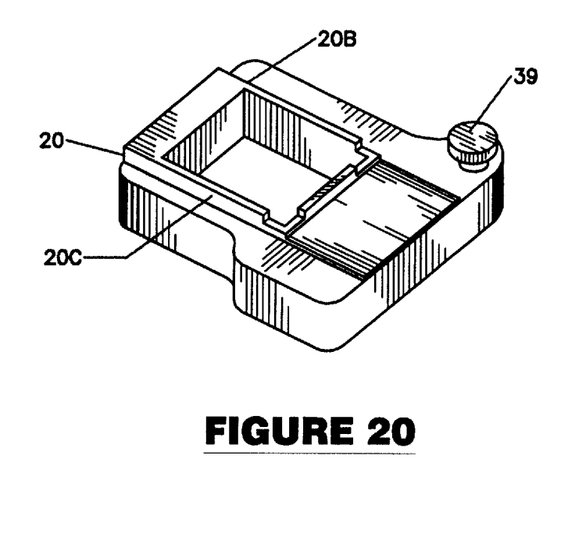
FIGS. 20–23 are various views illustrating the posterior stabilized collet portion of the preferred embodiment of the apparatus of the present invention.
Figure 21:
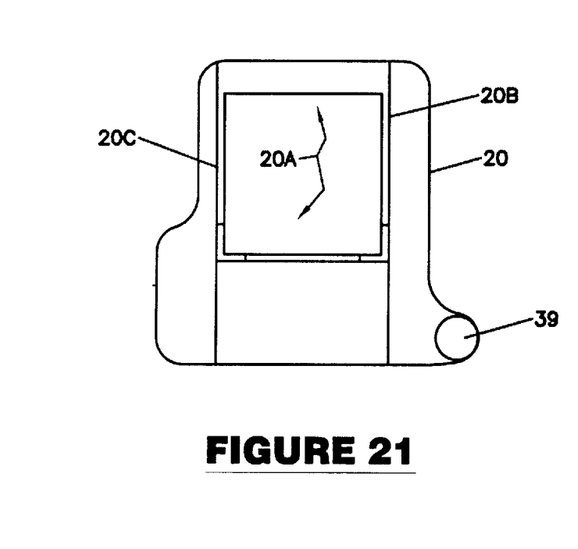
Figure 22:
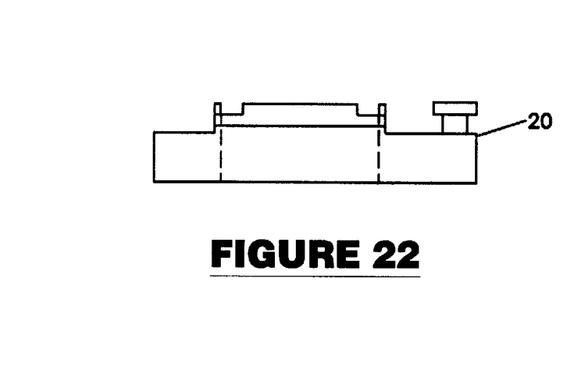
Figure 23:
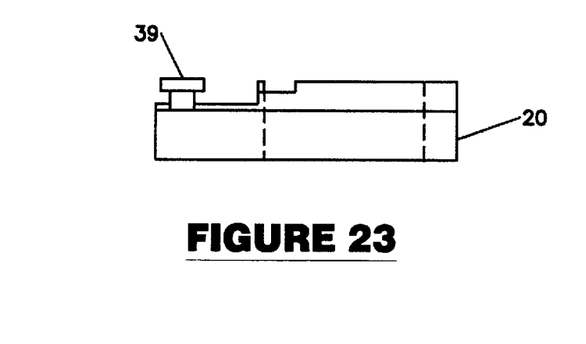
Figure 24:
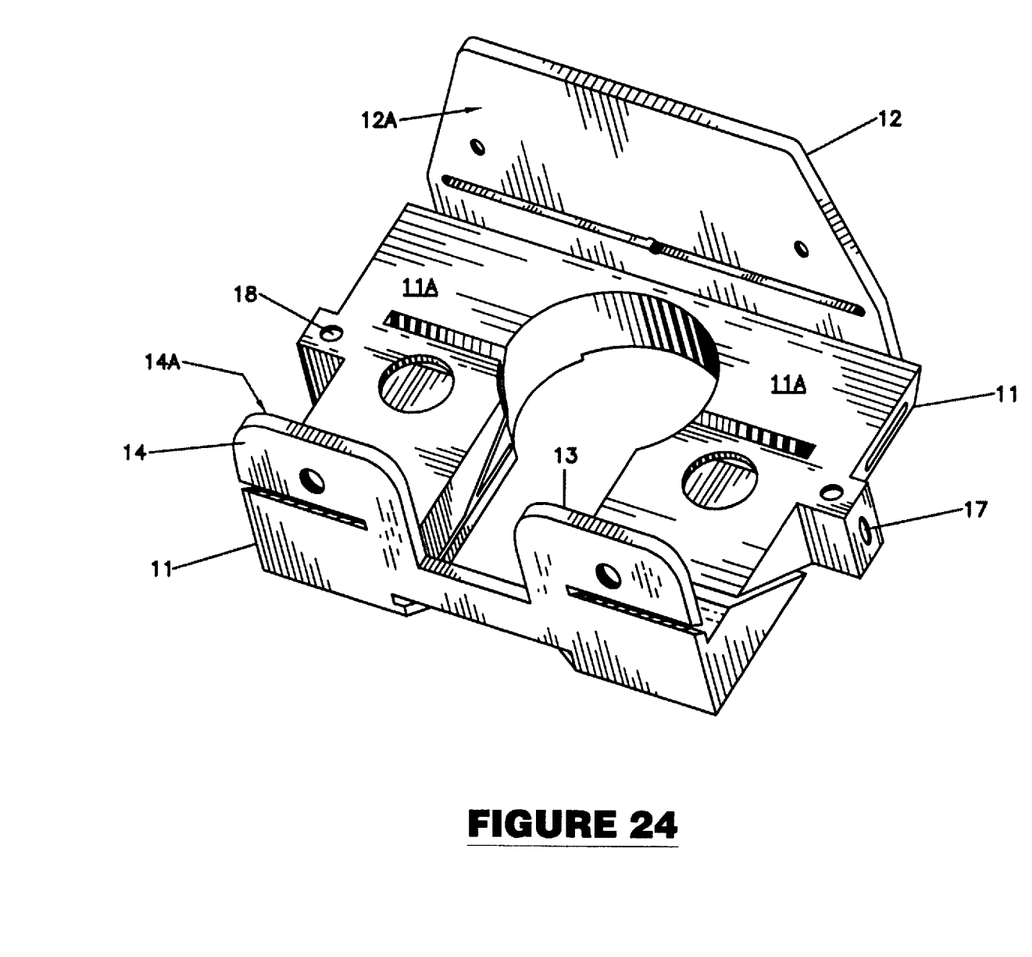
FIG. 24 is a perspective view of the block body portion of the preferred embodiment of the apparatus of the present invention.
Figure 25:
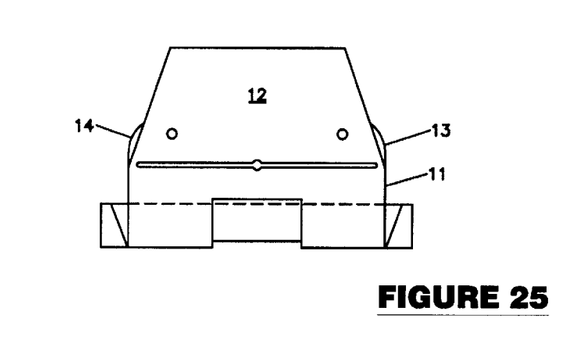
FIG. 25 is an anterior view of the block body of FIG. 24.
Figures 26, 27:
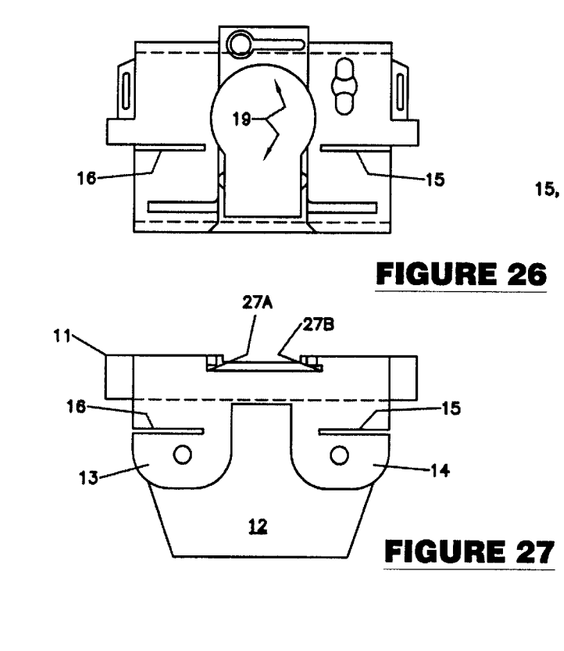
FIG. 26 is a proximal view of the block body of FIG. 24.
FIG. 27 is a posterior view of the block body of FIG. 24.
Figure 28:
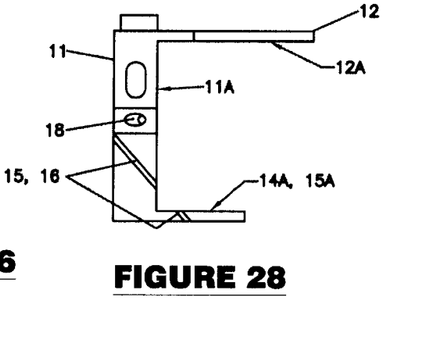
FIG. 28 is a side view of the block body of FIG. 24.

In revision cases, the surgeon attaches the modular stem 30 to block body 11 as shown in FIG. 11. This allows the surgeon to fasten additional modular stem portions (not shown) to the stem member 30 at externally threaded section 37. The stem 30 provides a large cylindrical section 35, a small cylindrical section 36, and externally threaded section 37. Other additional stem extension members that are internally threaded can thus be added to the stem 30 for increasing the length of the stem 30. The composite stem portion containing stem 30 and a selected stem extension or modular stem portion is then placed in the patient's intramedullary canal. This can be done before reaming is started on the patient's distal femur, using the embodiments shown in FIGS. 1–9.

A socket 43 can be provided for accepting a removal tool or hammer that aids in removing stem 30 from the patient's bone tissue if desired once block body 11 is connected to the patient's distal femur. Normally, the block body 11 and modular stem 30 would be placed in position on the patient's distal femur, using the stem 30 for orientation purposes. The surgeon will then pin the block body 11 to the distal femur using bone spikes for example that are placed through openings 17 and 18.

The surgeon will then remove the modular stem 30 by loosening the threaded fasteners 31 thus disengaging the modular stem 30 from the block body 11. A removal tool would then be inserted in the socket 43. The socket 43 and removal tool are needed to help pull the modular stem 30 from the patient's distal femur, through block body 11. After removal of the modular stem 30, reaming can begin using reamer 22, either of the collets 20 or 21 as desired and then a box chisel. The box chisel tracks the interior side walls of the selected collet 20 or 21 after reaming a slot using reamer 22.

PARTS LIST

| Part Number | Description |
| --- | --- |
| 10 | orthopaedic cutting instrument |
| 11 | block body |
| 11A | flat surface |
| 12 | anterior flange |
| 12A | flat surface |
| 13 | posterior flange |
| 13A | flat surface |
| 14 | posterior flange |
| 14A | flat surface |
| 15 | chamfer cutting slot |
| 16 | chamfer cutting slot |
| 17 | bone spike opening |
| 18 | bone spike opening |
| 19 | central open area |
| 19A | stop |
| 20 | p/s (posterior stabilized) collet |
| 20A | open center portion |
| 20B | side |
| 20C | side |
| 21 | constrained collet |
| 21A | open center portion |
| 21B | arrow |
| 22 | reamer |
| 23 | reamer stop |
| 24 | interface for driver |
| 25 | cutting end portion |
| 25A | cylindrical surface |
| 26A | rail |
| 26B | rail |
| 27A | slot |
| 27B | slot |
| 28 | slotted opening |
| 29 | internally threaded opening |
| 30 | modular stem |
| 31 | threaded fastener |
| 32 | threaded portion |
| 33 | key |
| 34 | distal end |
| 35 | smooth section |
| 36 | smaller diameter section |
| 37 | externally threaded section |
| 38 | slot |
| 39 | stud |
| 40 | circular opening |
| 41 | cylindrical opening |
| 42 | rectangular block portion |
| 43 | socket |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A cutting block instrument for cutting a patient's surgically cut distal femur to receive either a constrained or a posterior stabilized femoral prosthesis component after the distal femur has been surgically cut with at least three cuts including anterior, posterior, and distal cuts, said instrument comprising:

a) an instrument body having cutting guide surfaces that enable the surgeon to make anterior chamfer and posterior chamfer cuts on the patient's distal femur, said instrument body having flat surface portions for respectively engaging the anterior femoral cut, the posterior femoral cut and the distal femoral cut;

b) the instrument body including anterior and posterior flange portions that carry respectively the flat surface portions that engage the anterior and posterior cuts;

c) a recess on the instrument body that communicates with the distal femoral cut during use, said recess accepting either of a pair of collets that enable the surgeon to prepare the distal femur at the distal cut to receive either a posterior stabilized femoral prosthesis component or a constrained femoral prosthesis component;

d) each of the collets having an open center portion that is open to communicate with the distal femoral cut and with a reamer;

e) a rotary reamer that fits a selected of the collets at the open center portion thereof, said reamer having a stop that engages the collet to define a depth of cut during a reaming of the distal femur enabling a reamed opening to be formed in the distal femur;

f) the selected collet and reamer being movable together along the distal femur in a generally anterior-posterior direction during a reaming of the distal femur during use; and g) each of the collets having generally rectangular or square shape that enables the surgeon to track the collet with a box chisel during the formation of a rectangular or square cut into the distal femur, said rectangular or square cut being in communication with an opening reamed by the reamer.

2. The instrument of claim 1 further comprising a modular stem portion that fits the recess of the instrument body, said stem including an elongated portion that can track a patient's intramedullary canal and a proximal portion that attaches to the instrument body.

3. The instrument of claim 2 wherein the stem portion has a free end portion with a connection that enables the free end portion to accept a selected stem extensions.

4. The instrument of claim 2 wherein the stem portion has a free end portion that is threaded to accept a selected stem extensions.

5. The instrument of claim 1 wherein the collets are slidably affixed during use to different positions on the instrument body in a proximal to distal direction.

6. The instrument of claim 1 wherein the instrument body is generally "C" shaped having a distal member, an anterior member and a pair of posterior, condylar portions.

7. The instrument of claim 1 wherein the recess is open at one end portion thereof and closed at the other end portion thereof.

8. The instrument of claim 1 wherein the recess is open at the posterior end portion thereof and closed at the anterior end portion thereof.

9. The instrument of claim 1 wherein each collet is rectangular, comprised of four interior side wall portions that are guide surfaces for a box chisel.

10. The instrument of claim 1 wherein the reamer is an elongated member having a proximal end, a distal end and an annular shoulder between its ends that defines said stop.

11. A cutting block instrument for cutting a patient's surgically cut distal femur to receive either a constrained or a posterior stabilized femoral prosthesis component after the distal femur has been surgically cut with three cuts including anterior, posterior and distal cuts, said instrument comprising:

a) an instrument body having cutting guide surfaces that enable the surgeon to make anterior chamfer and posterior chamfer cuts on the patient's distal femur, said instrument body having flat surface portions for engaging the anterior femoral cut, the posterior femoral cut and the distal femoral cut;

b) the instrument body including anterior and posterior flange portions that carry respectively the flat surface portions that respectively engage the anterior and posterior cuts;

c) a recess on the instrument body that communicates with the distal femoral cut during use, said recess accepting either of a pair of collets that enable the surgeon to prepare the distal femur at the distal cut to receive either of a selected prosthesis that is a posterior stabilized femoral prosthesis component or a constrained femoral prosthesis component;

d) each of the collets having an open center portion that is open to communicate with the distal femoral cut and with a reamer;

e) a rotary reamer that fits the selected collet at the open center thereof, said reamer having a stop that engages the collet to define a depth of cut during a reaming of the distal femur to formed a reamed opening in the distal femur;

f) the selected collet and reamer being movable together along the distal femur in a generally anterior-posterior direction during a reaming of the distal femur during use;

g) each of the collets having generally rectangular or square shape that enables the surgeon to track the collet with a box chisel during the formation of a rectangular or square cut into the distal femur, said rectangular or square cut communication with an opening reamed by the reamer;

h) a stem portion that fits the recess of the instrument body, said stem including an elongated portion that can track a patient's intramedullary canal and a proximal portion that attaches to the instrument body;

i) wherein the stem can first track the patient's intramedullary canal independently of the instrument block body, thus enabling a surgeon to align the block body on the stem after the stem is placed in the intramedullary canal but before attaching the block body to the distal femur;

j) wherein the stem is removable from the instrument body after said alignment and said attachment of the block body to the distal femur.

12. A cutting block instrument for cutting a patient's surgically cut distal femur to receive either a constrained or a posterior stabilized femoral prosthesis component, said instrument comprising:

a) an instrument body including anterior and distal portions that carry flat surface portions that respectively engage the anterior and distal surface of the femur;

b) a recess on the instrument body that communicates with the distal femoral cut during use, said recess accepting either of a pair of collets that are configured differently in order to enable a surgeon to prepare the distal femur at the distal cut to receive either of a selected prosthesis that is a posterior stabilized femoral prosthesis component or a constrained femoral prosthesis component;

c) each of the collets having an open center portion that is open to receive a reamer; and d) a rotary reamer that fits the selected collet at the open center portion thereof for reaming of the distal femur to form a reamed opening in the distal femur;

e) the selected collet and reamer being movable together along the distal femur in a generally anterior-posterior direction during a reaming of the distal femur during use.

13. The instrument of claim 12 wherein each collet is movably mounted on the instrument body in an anterior to posterior direction.

14. The instrument of claim 12 wherein each collet has a generally rectangular open center portion for receiving a generally rectangular box chisel.

15. The instrument of claim 12 wherein a selected of the collets is slidably affixed to the instrument body during use.

16. The instrument of claim 12 further comprising a modular stem portion that fits the recess of the instrument body, said stem including an elongated portion that can track a patient's intramedullary canal and a proximal portion that attaches to the instrument body.

17. The instrument of claim 16 wherein the stem portion has a free end portion with a connection that enables the free end portion to accept a selected stem extension.

18. The instrument of claim 16 wherein the stem portion has a free end portion that is threaded to accept a selected stem extension.

19. The instrument of claim 12 wherein the collets are slidably affixed during use to different positions on the instrument body in a proximal to distal direction.

20. The instrument of claim 12 wherein the instrument body is generally "C" shaped having a distal member, an anterior member and a pair of posterior, condylar portions.

21. The instrument body of claim 12 wherein the recess is open at one end portion thereof and closed at the other end portion thereof.

22. The instrument body of claim 12 wherein the recess is open at the posterior end portion thereof and closed at the anterior end portion thereof.

23. The instrument body of claim 12 wherein each collet is rectangular, comprised of four interior side wall portions that are guide surfaces for a box chisel.

24. The instrument body of claim 12 wherein the reamer is an elongated member having a proximal end, a distal end and an annular shoulder between its ends that defines said stop.

* * * * *